(12) United States Patent
De Clerck

(10) Patent No.: US 8,251,698 B2
(45) Date of Patent: Aug. 28, 2012

(54) ORTHODONTIC IMPLANT

(76) Inventor: Hugo De Clerck, Tervuren (BE)

( * ) Notice: Subject to any disclaimer, the term of this patent is extended or adjusted under 35 U.S.C. 154(b) by 883 days.

(21) Appl. No.: 12/029,894

(22) Filed: Feb. 12, 2008

(65) Prior Publication Data
US 2008/0248441 A1 Oct. 9, 2008

Related U.S. Application Data

(63) Continuation-in-part of application No. 10/478,000, filed as application No. PCT/BE02/00082 on May 17, 2002, now Pat. No. 7,329,121.

(30) Foreign Application Priority Data

May 17, 2001 (BE) .................................. 2001/0343
Oct. 18, 2001 (BE) .................................. 2001/0673

(51) Int. Cl.
*A61C 3/00* (2006.01)

(52) U.S. Cl. ......................................................... 433/18

(58) Field of Classification Search .............. 433/17–24, 433/173, 174, 176; 623/17.17–17.19; 606/61, 606/70
See application file for complete search history.

(56) References Cited

U.S. PATENT DOCUMENTS

| 4,459,111 | A | 7/1984 | Valen |
| 5,123,838 | A | 6/1992 | Cannon |
| 5,853,291 | A * | 12/1998 | DeVincenzo et al. ........ 433/176 |
| 6,193,509 | B1 | 2/2001 | DeVincenzo |
| 6,827,574 | B2 * | 12/2004 | Payton .............................. 433/8 |
| 7,927,098 | B2 * | 4/2011 | Knopfle ........................... 433/18 |

FOREIGN PATENT DOCUMENTS

EP 0 947 177 10/1999
WO WO 01/82822 11/2001

* cited by examiner

*Primary Examiner* — Sunil K Singh
(74) *Attorney, Agent, or Firm* — Browdy and Neimark, PLLC

(57) ABSTRACT

Implant with fastening means (2) to be fixed to the bone of a person's upper jaw (5) or lower jaw (30), with a mounting element (3) for mounting orthodontic appliances, whereby said mounting element (3) is connected to fastening means (2) by means of a connecting piece (4) formed by a rod with a circular section or an elliptic section, which is adapted to extend through the person's gum surrounding the corresponding bone to which said fastening means (2) are intended to be fixed, whereby said fastening means (2) are formed of an osteosynthesis plate which is provided with several recesses (6,7,8,9) through which fit screws (10,11,12,13) for fixing the implant to the bone of said upper or lower jaw, wherein said connecting piece (4) forms an extension of the osteosynthesis plate.

7 Claims, 9 Drawing Sheets

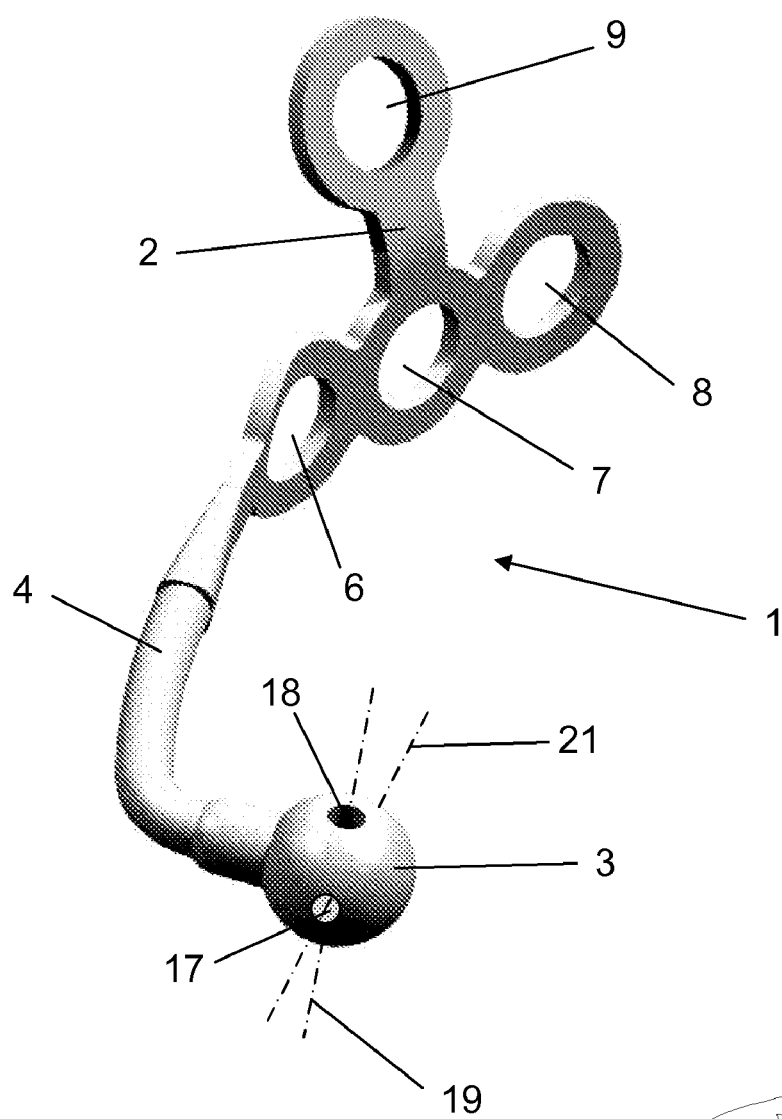
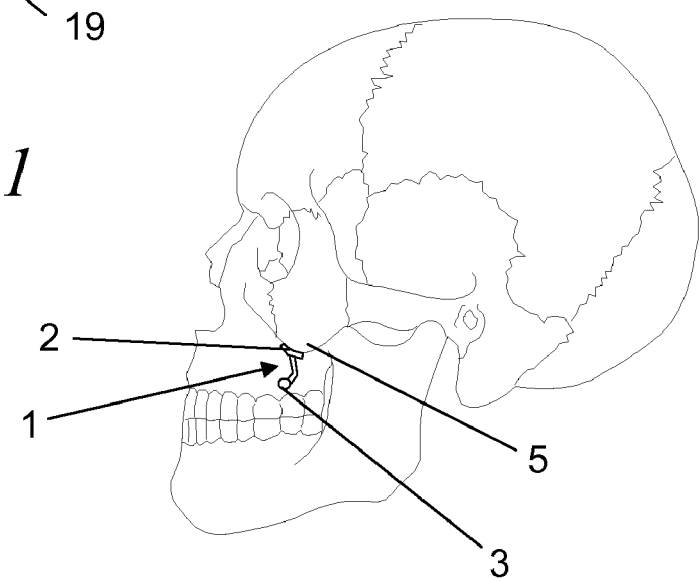
Fig. 1
Fig. 2

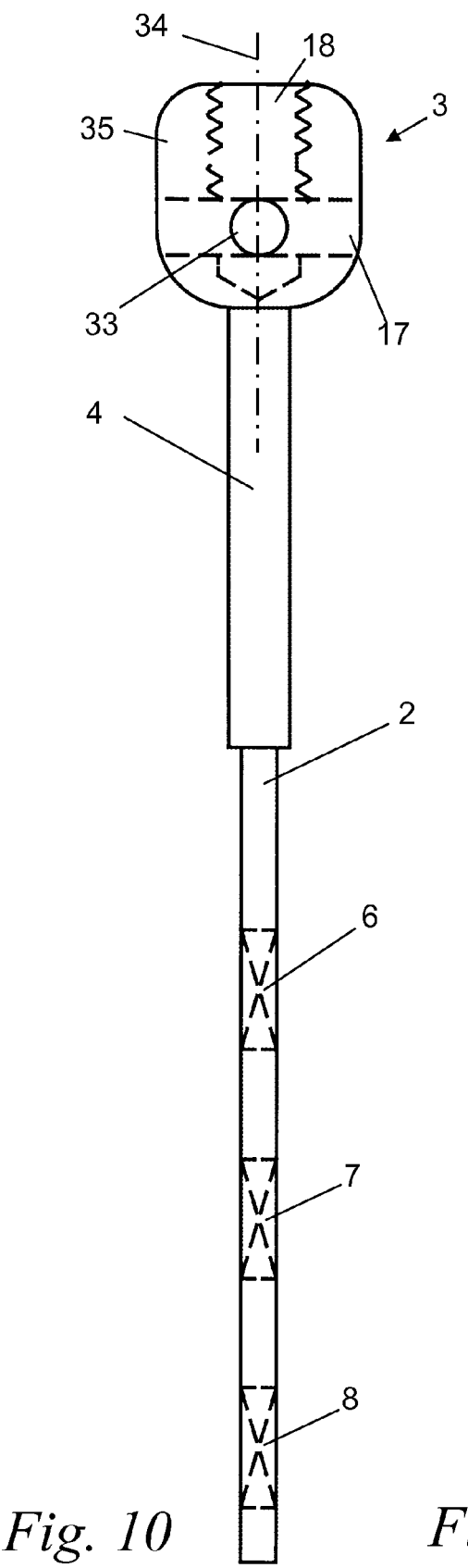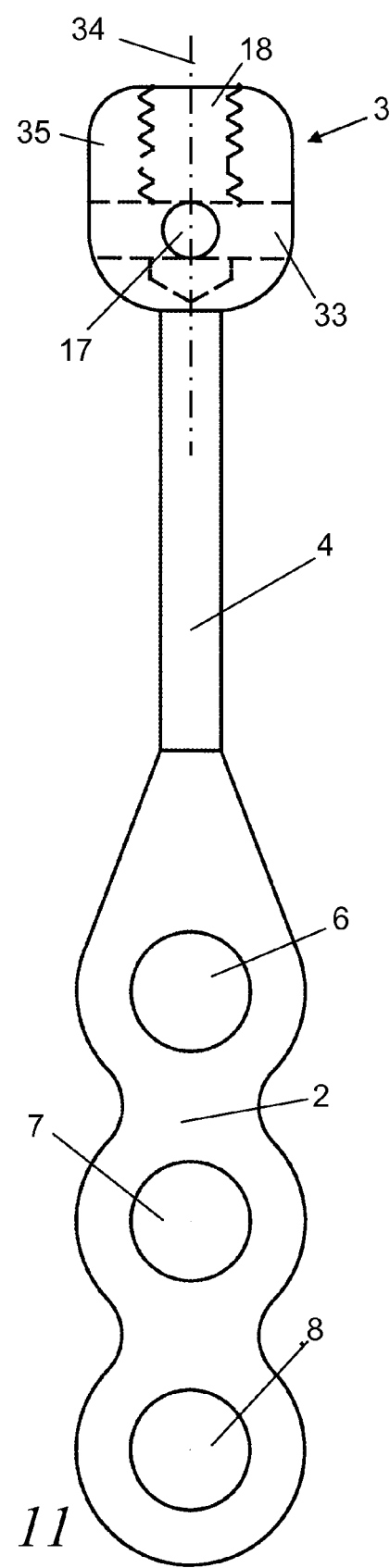

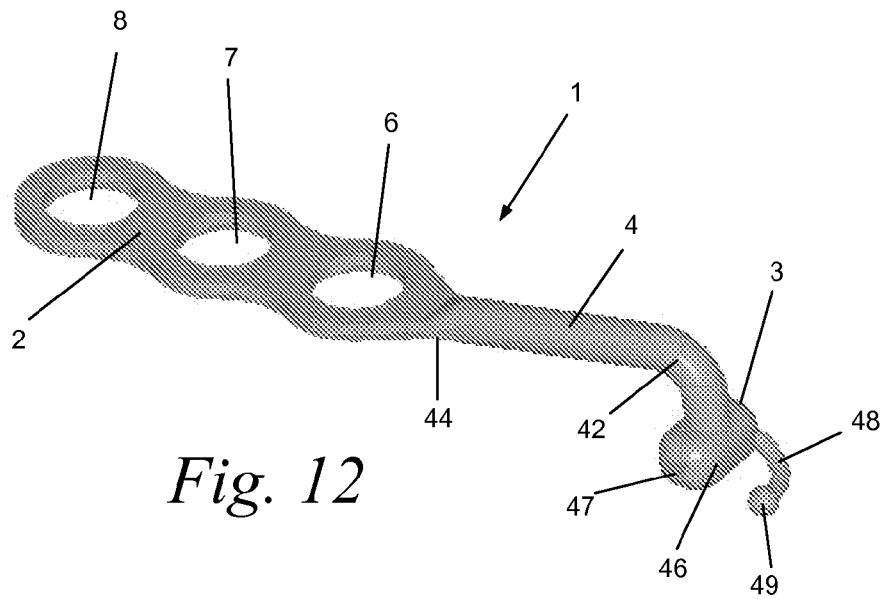
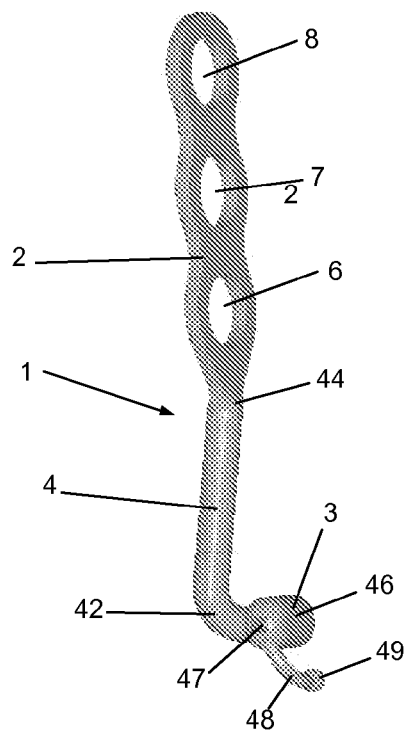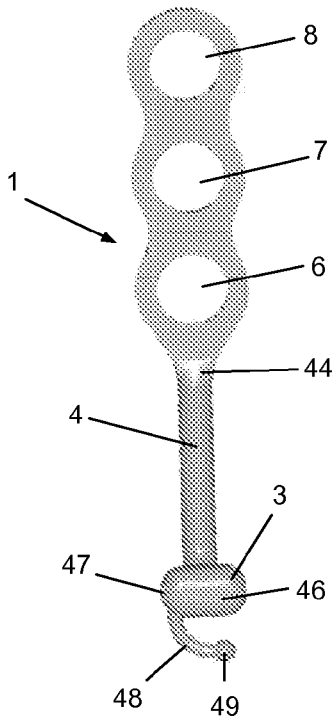
Fig. 12
Fig. 13        Fig. 14

ORTHODONTIC IMPLANT

The present application is a continuation-in-part of prior U.S. application Ser. No. 10/478,000, filed Nov. 17, 2003, now U.S. Pat. No. 7,329,121, issued Feb. 12, 2008, the entire contents of which are hereby incorporated by reference.

The present invention concerns an orthodontic implant which makes it possible to gradually move a person's teeth showing an incorrect implantation into an adjusted position by exerting an almost continuous pressure force or tensile force on these teeth.

The means used according to the present state of the art for thus adjusting the position of a person's teeth comprise different sorts of braces which can be placed in an either or not removable manner in a person's mouth. For some persons, what is called an outer brace is moreover required, which exerts an additional force on the person's teeth or on the upper or lower jaw, for example via the neck.

Such braces are particularly unpleasant to wear and they do not always make it possible to obtain a precise, reproducible distribution of power on the person's teeth or jaw.

The document U.S. Pat. No. 5,853,291 of De Vincenzo discloses an implant with a flat base that has to be fixed to the jawbone and a connecting piece that is extending perpendicular to this base. The device of De Vincenzo has to be positioned between or at least in the neighbourhood of the roots of the teeth. Accordingly, these roots may be damaged such that there is always a risk that these teeth are damaged and will be lost.

The invention aims to remedy these disadvantages by proposing an orthodontic implant which makes it possible to change the position of a person's teeth in a simple and precise manner. When using an implant according to the invention, the use of an outer brace is no longer required, and remarkably good results are obtained. Moreover the roots of the teeth cannot be damaged by the use of the implant, according to the invention.

To this aim, the orthodontic implant according to the invention has fastening means to be fixed to the bone of a person's upper jaw or lower jaw, and it further comprises a mounting element for mounting orthodontic appliances, whereby said mounting element is connected to the above-mentioned fastening means by means of a connecting piece which must extend through the gum surrounding the corresponding bone.

The connecting piece has a circular section or an elliptic section and forms an extension of the fastening means, whereby the longitudinal axis of this connecting piece is, in an advantageous manner, a tangent to a plate that is forming the fastening means. The fastening means are preferably formed of an osteosynthesis plate which is provided with several recesses through which fit, for example, screws for fixing the implant to the bone of said upper or lower jaw and whereby said connecting piece forms an extension of the osteosynthesis plate.

Practically, said mounting element contains at least one bore hole which is provided with thread co-operating with a bolt which makes it possible to fix said appliances to the implant.

Preferably, at least some of said recesses provided in the osteosynthesis plate successively extend according to a longitudinal direction of said connecting piece.

According to a preferred embodiment of the implant according to the invention, said connecting piece presents at least a first bend, this first bend forming a support for the connecting piece against the jawbone when the implant is fixed to this jawbone.

Further, a second bend in the connecting piece can be provided. This second bend is extending in a direction opposite to said first bend and provided between this first bend and said recesses such that when the implant is fixed to the jawbone a free space is maintained between this second bend and the jawbone.

According to a further embodiment of the implant according to the invention, said mounting element has at least one recess in which a corresponding coupling element of said appliances is to be mounted.

According to a special embodiment of the implant according to the invention, said connecting piece is bent in order to make sure that the longitudinal axis of said recess extends almost parallel to the lateral surfaces of the teeth situated in the jaw upon which said implant must be fixed.

According to an advantageous embodiment of the implant according to the invention, said fastening means are formed of a plate which is provided with one or several recesses through which screws fit for fixing the implant to the bone of said upper or lower jaw.

In an advantageous manner, the above-mentioned mounting element is at least partially spherical.

According to an interesting embodiment of the implant according to the invention, the above-mentioned connecting piece has a cross section with round angles, or a circular or elliptic cross section.

The invention is also relating to a method for fixing said implant to a jawbone, wherein an incision is made in a person's gum and wherein the fastening means are fixed to the underlying jawbone at a position that is at least partly covered by movable mucosa whereby the implant is positioned such that the connecting piece is piercing the gum in the neighbourhood of the teeth at a position of the jawbone that is covered by attached gingiva. The gum around the connecting piece and the fastening means is sutured after fixing the fastening means such that the mounting element protrudes in the oral cavity.

Other particularities and advantages of the invention will become clear from the following description of a few specific embodiments of the implant according to the invention; this description is given as an example only and does not restrict the scope of the claimed protection in any way; the reference figures used hereafter refer to the accompanying drawings.

FIG. 1 is a schematic view in perspective of the implant according to the invention.

FIG. 2 is a schematic side view of a skull where the implant according to the invention is fixed to the upper jaw.

FIG. 10 is a schematic side view of an implant according to another embodiment of the invention.

FIG. 11 is a schematic front view of the implant from FIG. 10.

In the different drawings, the same reference figures refer to identical or analogous elements.

FIG. 12 is a schematic view in perspective of an implant according to a preferred embodiment of the invention.

FIG. 13 is a schematic front view of the implant from FIG. 12.

FIG. 14 is a schematic lateral view in perspective of the implant from FIG. 12.

Figure 15:
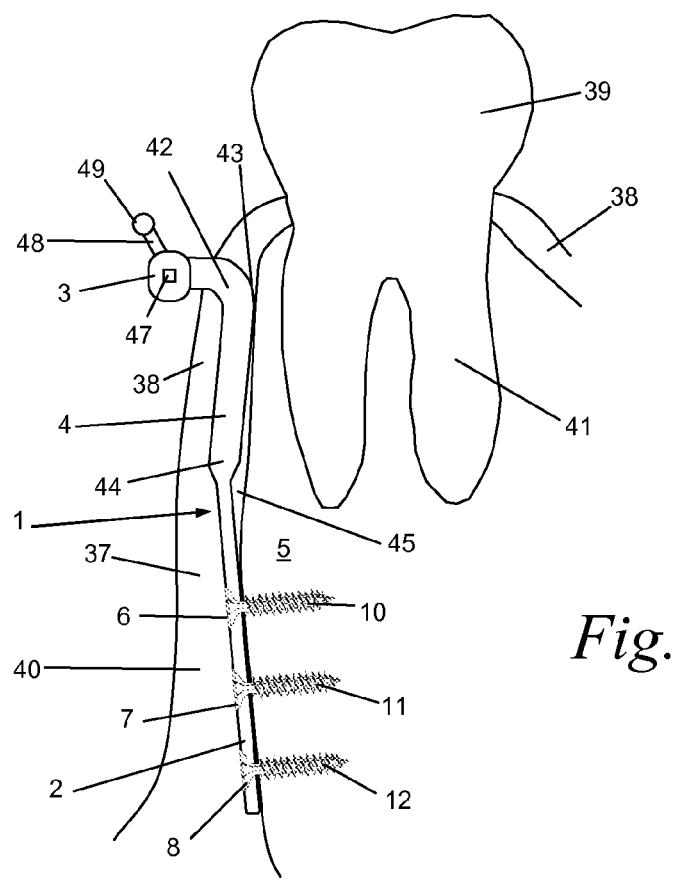

FIG. 15 is a schematic cross section of a lower jaw with the implant represented in FIGS. 12 to 13.

Figure 16:
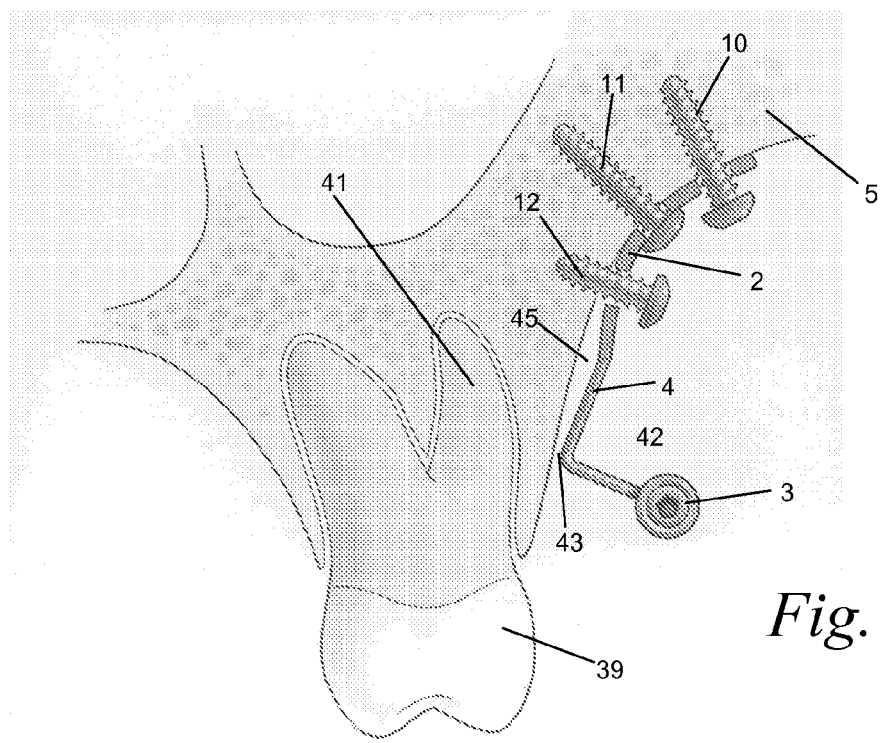

FIG. 16 is a schematic cross section of an upper jaw with an implant according to the invention.

FIGS. 17a to 17e represent successive steps in a method, according to the invention for fixing an implant, according to the invention, to a jawbone The invention in general concerns an orthodontic implant which makes it possible to connect orthodontic appliances, such as for example fixed braces, to the bone of a person's upper or lower jaw and to a method for fixing such an implant to the jawbone.

Fixed braces are known as such. With such braces, what are called brackets are fixed to the teeth. These brackets are mutually connected via a metal wire which makes it possible to exert an almost continuous force on the brackets so as to move certain teeth gradually into an adjusted position.

The implant according to the invention is connected to this wire, or to one or several brackets, via a coupling element so as to exert a suitable force in order to adjust the position of the corresponding teeth.

FIG. 1 represents a specific embodiment of an orthodontic implant according to the invention. This implant 1 has fastening means 2 to be fixed to the bone of an upper or lower jaw and a mounting element 3 for connecting orthodontic appliances to the implant 1.

The fastening means 2 and the mounting element 3 are connected to one another via a connecting piece in the shape of a rod 4 with a circular cross section.

Figure 3:
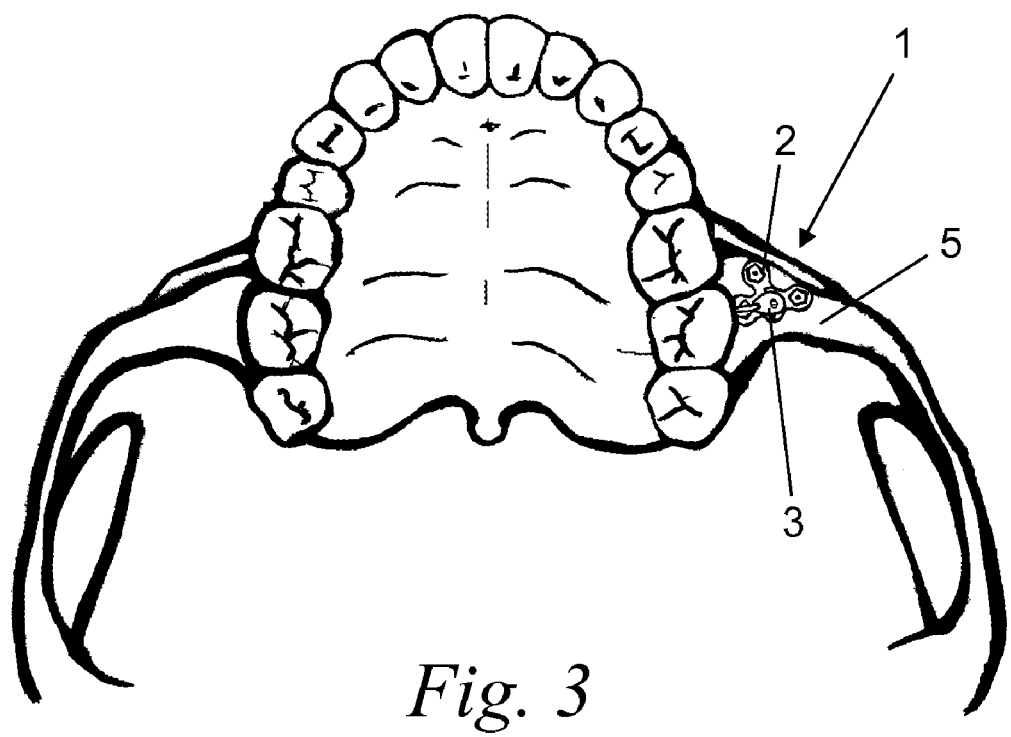
FIG. 3 is a schematic bottom view of an upper jaw onto which the implant according to the invention is attached.

This implant 1 is fixed to the bone of a person's upper jaw 5 by means of the above-mentioned fastening means 2, as is represented in FIGS. 2 and 3.

Thus, the fastening means 2 have a T-shaped osteosynthesis plate with four circular recesses 6, 7, 8 and 9. Through these recesses fit corresponding screws 10, 11, 12 and 13 for fixing the fastening means 2 tight to the bone of the jaw 5.

As is clearly represented in FIG. 3, the fastening means 2 make it possible to fix the implant 1 to the lower side of the bone connecting the upper jaw 5 to what is called the zygoma. To this end, said osteosynthesis plate is preferably slightly bent.

Said rod 4, forming the connecting piece between the fastening means 2 and the mounting element 3, extends through the gum surrounding the jawbone 5, such that the mounting element 3 is situated in the oral cavity between the jawbone and the cheek. For clarity's sake, the gum is not represented in the FIGS. 2 to 7.

In order to obtain a tight connection between the rod 4 and the gum, and in order to make sure that the latter does not get irritated by the rod 4, it has a cross section with round edges, and this section is preferably circular. According to an advantageous embodiment, the rod 4 has a smaller diameter than the mounting element 3.

In an advantageous manner, the mounting element 3 is made spherical or drop-shaped at least on the side of the rod 4. As this has for a result that there are no sharp edges which could get into contact with the lips, the cheeks or the gum, the formation of wounds therein is avoided. Preferably, however, the entire mounting element 3 is made spherical or drop-shaped.

Figure 5:
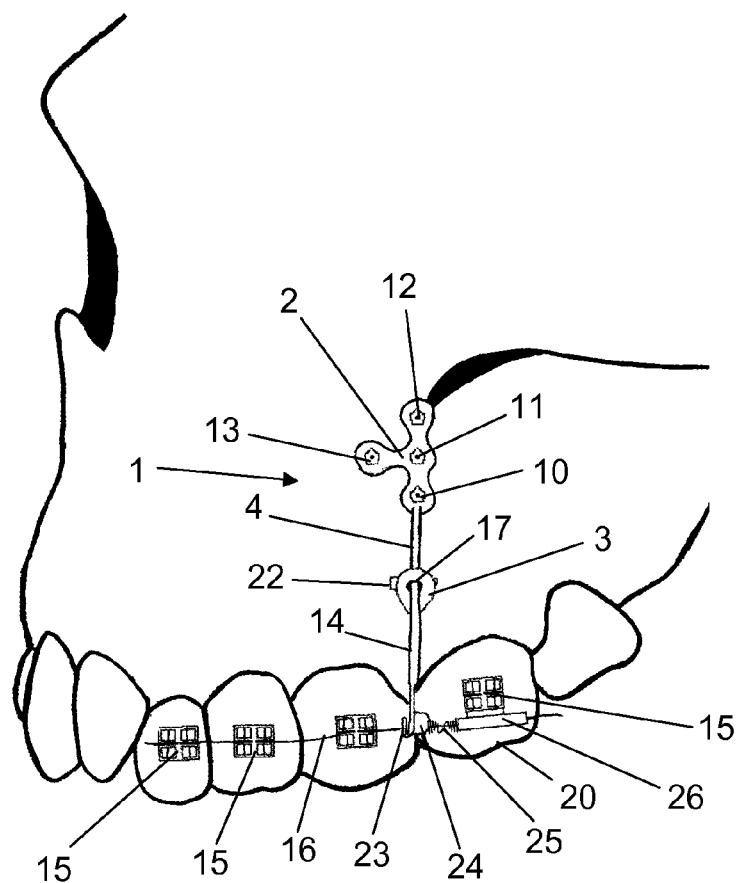
FIG. 5 is a schematic side view of part of an upper jaw provided with the implant according to the invention, with orthodontic appliances.

Via this mounting element 3, said orthodontic appliances are fixed to the implant. FIG. 5 thus schematically represents an implant 1 which is connected via a coupling element, in particular a tie-bar 14, to a fixed brace containing a number of brackets 15 which are each fixed to a tooth 20 and which are connected to a metal wire 16 in a manner known as such.

The tie-bar 14 is fixed to the mounting element 3 of the implant 1 via one end. To this end, the mounting element 3 has a longitudinal, preferably cylindrical recess 17 in which said far end of the tie-bar 14 fits.

In order to fix the tie-bar 14 tight to the mounting element 3, the latter is provided with a cylindrical bore hole 18 in which is provided a thread co-operating with a bolt 22. The axis 19 of the bore hole 18 extends almost perpendicular to the axis 21 of the recess 17 and intersects the latter, such that, by means of said bolt 22, the tie-bar 14 can be clamped in said recess 17.

In order to make sure that the tie-bar 14 cannot rotate in relation to its axis, it will preferably have a cross section in the shape of a right-angled quadrangle. Thus, the bolt 22 pushes with its flat end against a lateral surface of the tie-bar 14 which is mounted in the cylindrical recess 17, and it is thus clamped tight in the latter.

According to an advantageous embodiment of the implant according to the invention, said rod 4 is bent, so that the axis 21 of said recess 17 extends almost parallel to the lateral surfaces of the teeth 20 situated in the jaw upon which the implant 1 is fixed.

Thus, the axis 21 of this recess 17 extends for example at an angle between some 60° and 150° in relation to the fastening means 2.

According to a preferred embodiment of the implant according to the invention, said tie-bar 14 has an eye at its far end which is to be fixed in said recess 17, such that the bolt 22 situated in the bore hole 18 extends through this eye, as a result of which the tie-bar 14 is fixed tight to the mounting element 3.

The cross section of the tie-bar 14, as well as that of the recess 17, can have all sorts of shapes and can for example be circular or hexagonal.

The free end of the tie-bar 14 has a hook 23 through which said metal wire 16 extends. The hook 23 presses against a round disc 24 which is coaxial to said wire 16 and which can move according to the longitudinal direction of the latter.

Further, a spiral compression spring 25 is provided which is coaxial to said metal wire 16 as well, and which pushes against said disc 24 on the one hand, and against a tubular element 26 of a bracket 15 on the other hand. In this manner, an almost continuous pressure force is exerted via the implant 1 on the corresponding tooth 20, to which the concerned bracket is attached.

Figure 6:
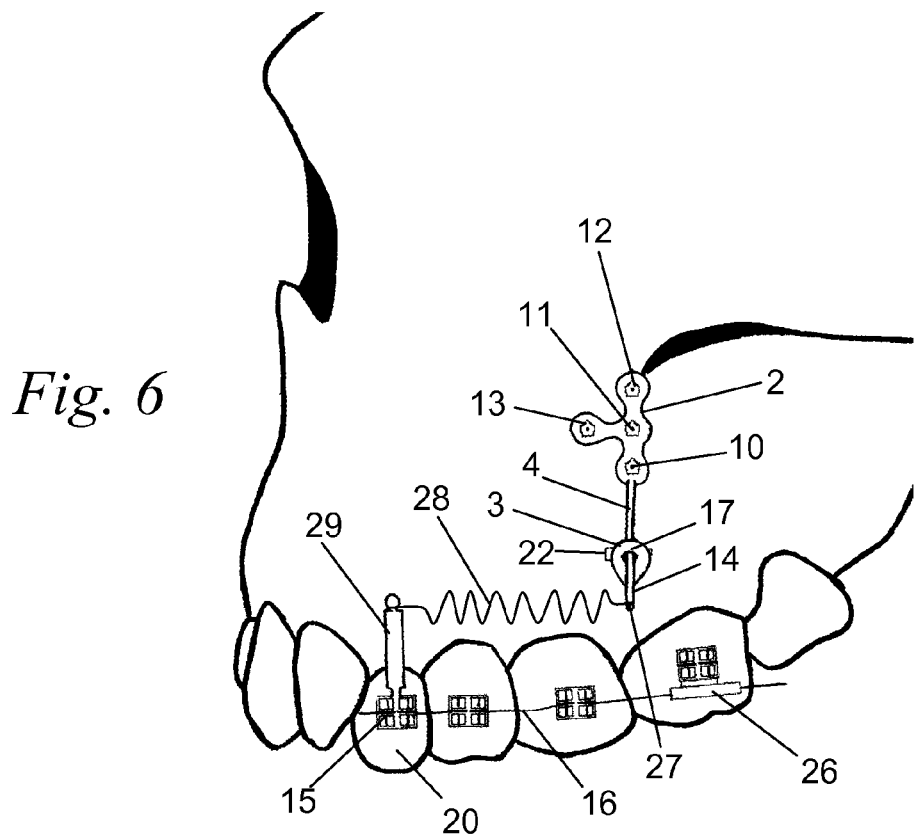
FIG. 6 is a schematic side view of part of an upper jaw provided with the implant according to the invention, with different orthodontic appliances.

FIG. 6 represents another application of the implant according to the invention, whereby a tensile force is exerted on a tooth 20. A tie-bar 14 is hereby fixed in said recess 17 of the mounting element 3. On the free end 27 of this tie-bar 14 is attached a spiral draw spring 28 which is connected to a tension member 29 cooperating with a bracket 15 which is fixed to a tooth 20. Thus, via the implant 1 is exerted a tensile force on this tooth 20 which makes sure that the position of the latter is gradually adjusted.

According to a variant of this embodiment, the spiral spring 28 can for example be connected directly to the mounting element 3, and the use of a tie-bar is not required.

Possibly, the spiral spring 28 can be replaced by another element exerting a tensile force, such as for example a rubber band.

Naturally, the implant according to the invention is preferably made of a bio-compatible material, such as for example titanium.

In the accompanying figures, the orthodontic implant 1 is attached to the jaw near a person's rear molars. However, it is also possible to fix it to other places on the jaw bone. To this end, the shape of said osteosynthesis plate will possibly have to be adjusted to the bone concerned, and it may be necessary to change the length and shape of the above-mentioned connecting piece correspondingly.

Figure 4:
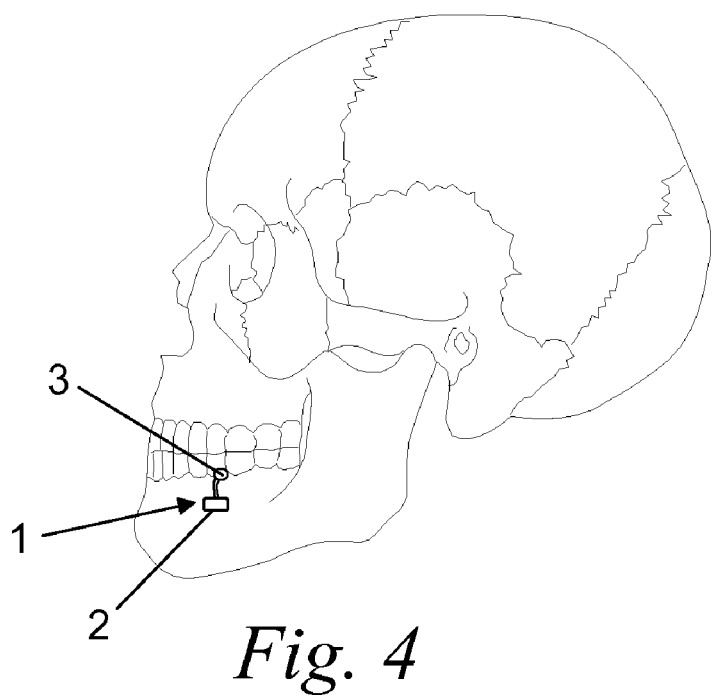
FIG. 4 is a schematic side view of a skull where the implant according to the invention is fixed to the lower jaw.

FIG. 4 is a schematic representation of the orthodontic implant according to the invention when fixed to the lower jaw. In this case, the shape of said osteosynthesis plate is adjusted such that it can be connected to the bone of the lower jaw where it is to be mounted.

Figure 7:
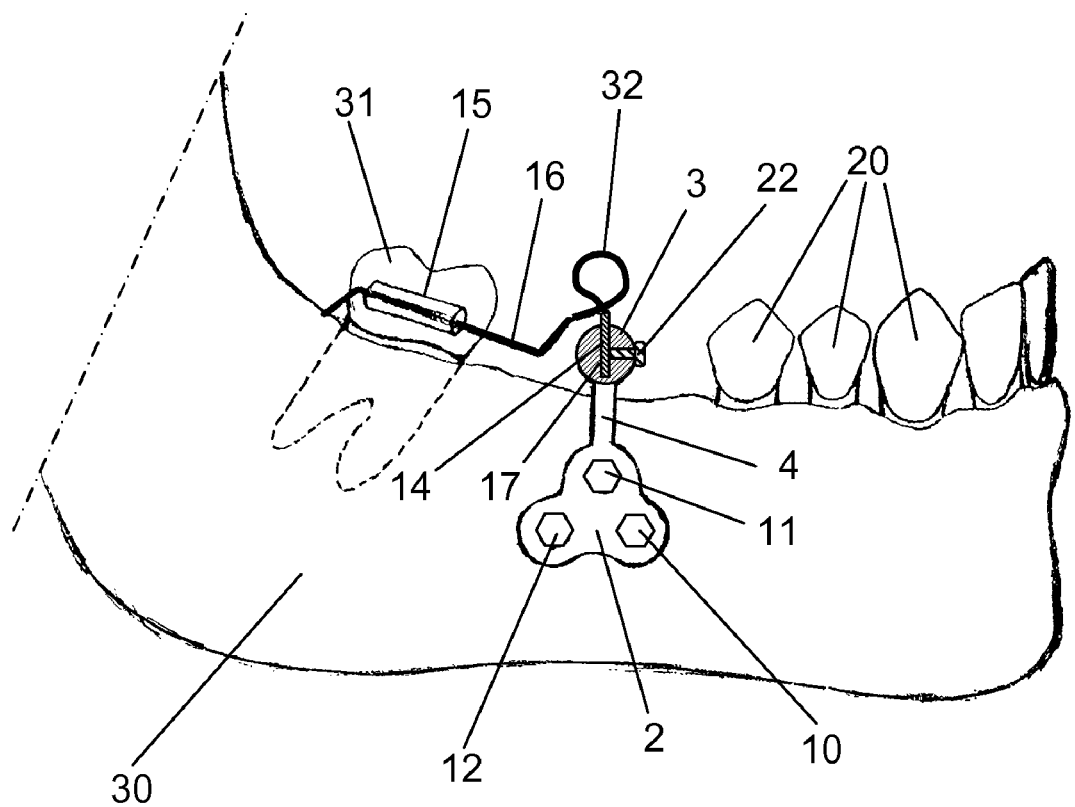
FIG. 7 is a schematic side view of part of a lower jaw which is provided with an orthodontic implant according to the invention.

FIG. 7 is a schematic side view of a lower jaw 30 whereby the orthodontic implant according to the invention is attached to the jaw bone in order to raise a molar 31 from the represented toppled position. This implant has fastening means 2 in the shape of an osteosynthesis plate with three recesses through which a screw 10, 11 and 12 extends each time in order to fix the implant 1 to the lower jaw 30. Further, a connecting rod 4 extends up to a spherical mounting element 3. The latter is represented as a cross section and has a bore hole 18 opening into a cylindrical recess 17 which extends almost crosswise to said bore hole 18. Thus, a coupling element can be fixed in the recess 17 via a bolt 22 provided in the bore hole. This coupling element consists of a tie-bar 14 and is mounted in said recess 17 with one far end, whereas the other far end is equipped with a spiral spring 32.

The central axis of the recess of the mounting element 3 preferably extends almost parallel to the fastening means 2 and to the lateral surfaces of the teeth 20 of the lower jaw 30.

The tie-bar 14 has a flat side on the far end situated in the recess 17, whereby the bolt 22 pushes against this side, such that the tie-bar 14 is fixed in the mounting element 3. On the far end situated in the recess 17, the tie-bar 14 preferably has four flat sides, and, consequently, it has a quadrangular cross section allowing us to fix it in different positions in the mounting element 14.

The spiral spring 32 is further connected to a relatively rigid wire 16 cooperating with the latter via a bracket 15 which is attached to the molar 31 to be raised. Thus, the spiral spring 32 exerts an almost continuous pressure force on the molar 31, and it is gradually raised in relation to the lower jaw 30.

Figures 8, 9:
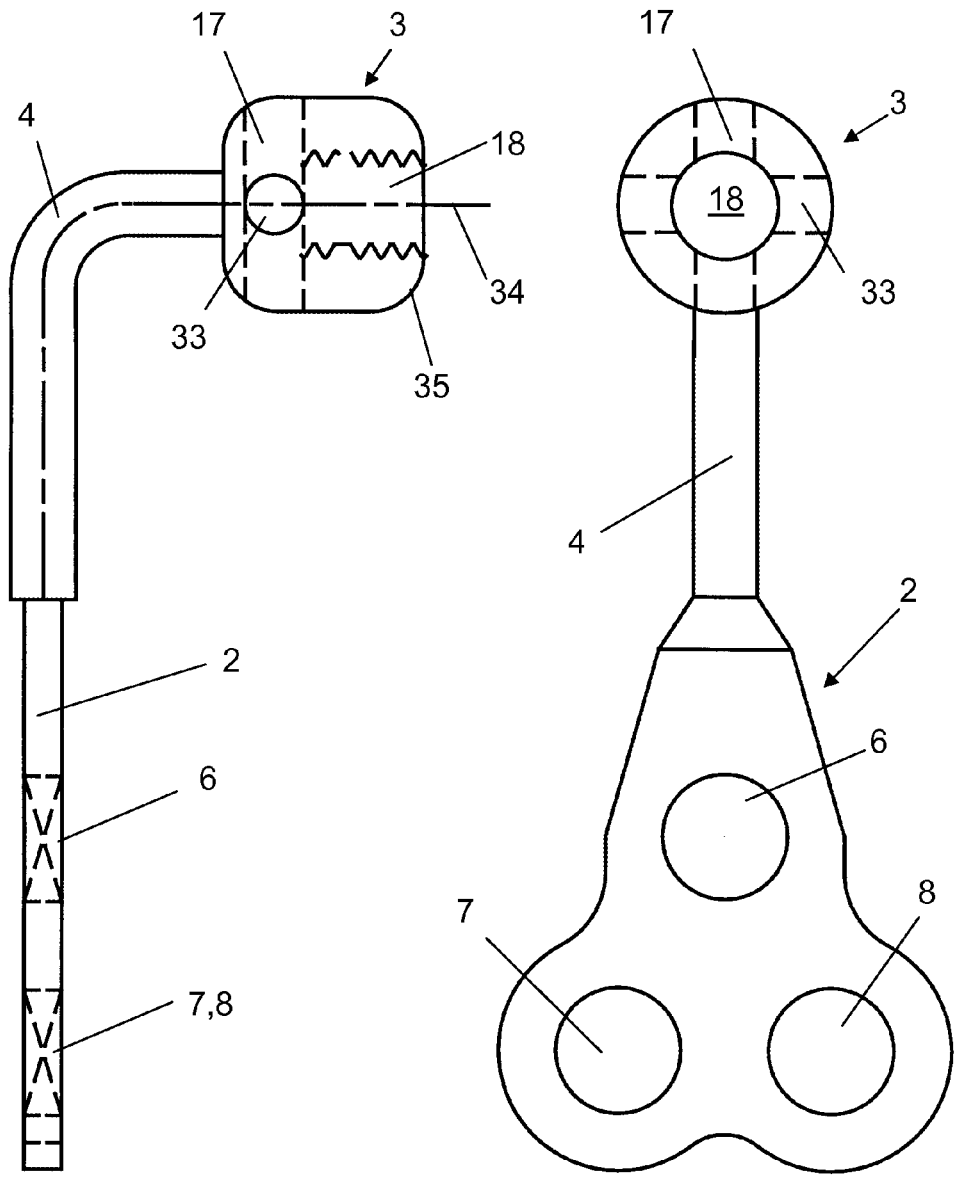
FIG. 8 is a schematic side view of an implant according to an interesting embodiment of the invention.
FIG. 9 is a schematic front view of the implant from FIG. 8.

FIGS. 8 and 9 schematically represent a very interesting embodiment of the implant according to the invention. This embodiment differs among others from the above-described embodiments in that the mounting element 3 is cylindrical, whereby it is coaxial to the rod 4 which is bent over an angle of for example 90°.

This mounting element 3 has two cylindrical recesses 17 and 33 which extend crosswise to the longitudinal axis 34 thereof, and which are almost perpendicular in relation to one another. Further, the mounting element 3 is provided with a threaded bore hole 18 which is coaxial to the mounting element 3, and which extends between said recesses 17 and 33 and the lateral surface 35 of the mounting element 3 situated opposite to said rod 4. Thus, it is possible to fix orthodontic appliances, such as a tie-bar, in one of the recesses 17 or 33 by means of a bolt which is screwed in the bore hole 18.

Such a mounting element 3 makes it possible, among others, to fix orthodontic appliances in different directions, depending on the used recess 17 or 33. Moreover, this mounting element 3 offers a major advantage in that said bore hole 18 extends substantially cross-wise to the lateral surfaces of the teeth, after the implant has been fixed to a jaw, such that this bore hole 18 is easily accessible in the oral cavity for screwing a bolt in it.

Further, the implant according to this embodiment of the invention has fastening means 2 in the shape of an osteosynthesis plate with three circular recesses 6, 7 and 8 for fixing the implant to a person's upper or lower jaw by means of corresponding screws.

In an advantageous manner, the fastening means 2 are made of a resorbent material, in particular such as for example a resorbent polymer containing L-lactide, D-lactide and Glycolide in a molecular ratio of 85/5/10, whereas the mounting element 3 and the rod 4 are made for example of titanium.

This rod 4 is then connected to the fastening means 2 by means of a screwed joint, for example. After the teeth have been put into an adjusted position, the rod 4 with the mounting element 3 is detached from the fastening means 2, for example by loosening the rod 4, and it is thus removed. It is not required then, to remove the fastening means 2, since they have been entirely resorbed after for example one to two years.

In a very advantageous manner, apart from the fastening means 2, also the mounting element 3 and the rod 4 are made of a resorbent material.

In a manner which is also very advantageous, the fastening means 2, the mounting element 3 and the rod 4 are made in one piece, and they are made for example of a resorbent material. After the teeth have been put into an adjusted position, the rod 4 with the mounting element 3 is detached from the fastening means 2, for example by breaking off the rod 4 or by cutting it through, and it is thus removed.

The embodiment of the implant according to the invention, as is represented in FIGS. 10 and 11, differs from the preceding embodiment in that the rod 4 is not bent. This rod 4 is made such that it can be bent in the required position by heating it, for example. Further, the circular recesses 6, 7 and 8, which are provided in the osteosynthesis plate 2, extend according to the longitudinal axis of the rod 4 which coincides with the rod 34 of the mounting element 3.

It is clear that, according to the invention, the embodiment of the implant as represented in FIGS. 8 and 9, can also be made with a rod 4 which is not bent, such as in the embodiment of the implant as represented in FIGS. 10 and 11.

It is also clear that, in order to avoid wounds being formed in the oral cavity, the mounting element 3 has round angles.

Figure 17A:
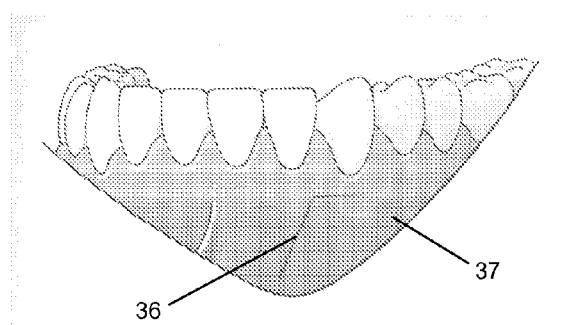
Figure 17B:
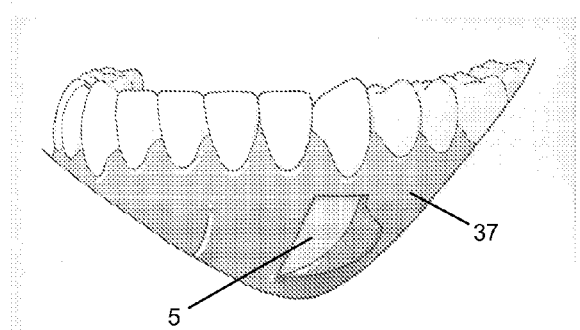
Figure 17C:
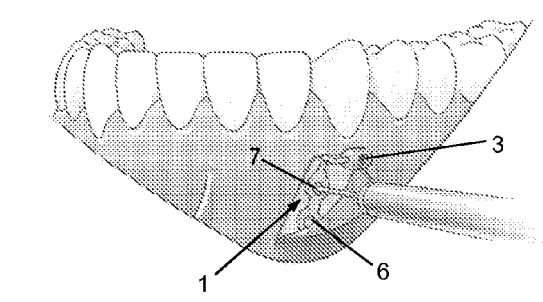
Figure 17D:
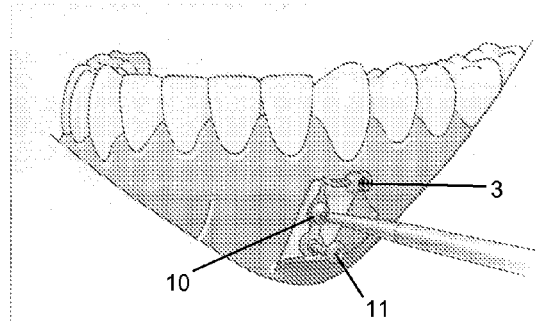
Figure 17E:
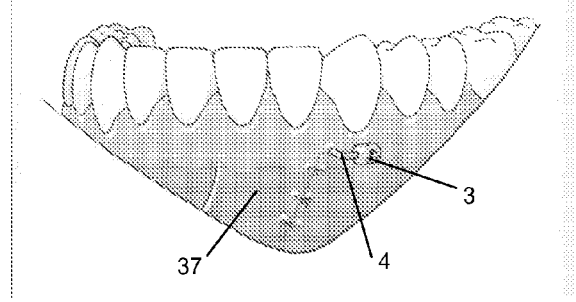

The placing of the implant according to the invention on the lower or upper jaw only requires a small surgical treatment. A small incision 36 is made in the gum 37 under local anaesthesia on the spot where the implant 1 has to extend through the gum as represented in FIGS. 17a and 17b. The implant 1 is hold on its desired position and boreholes are made through the recesses 6 and 7 of the implant 1 into the bone 5 of the jaw as shown schematically in FIG. 17c. Next, the fastening means 2 are fixed to the underlying jaw bone 5 by means of screws 10 and 11 and a screwdriver as represented in FIG. 17d. As shown in FIG. 17e, the gum 37 around the connecting piece 4 is then sutured, such that the connecting piece 4 pierces the gum 37 and the mounting element 3 protrudes in the oral cavity. The orthodontic appliances are preferably only connected to this mounting element 3 after the gum 37 has healed and the screws with which the implant has been fixed have sufficiently knitted together with the bone.

According to the invention, said incision is made in a person's gum 37 is extending from the attached gingiva 38 in the neighbourhood of the teeth 39 up to a part of the movable mucosa 40, or the so-called alveolar mucosa. The fastening means 2 of the implant 1 are fixed to the underlying jawbone 5 at a position that is at least partly covered by movable mucosa 40 whereby the implant is positioned such that the connecting piece 4 is piercing the gum 37 in the neighbourhood of the teeth 39 at a position of the jawbone 5 that is covered by attached gingiva 38. This is schematically represented in FIG. 15. The fastening means 2 are thus positioned beneath the roots 41 of the teeth 39 of the lower jaw or above the teeth 39 of the upper jaw as can be clearly seen from the FIGS. 15 and 16.

In this way it is possible to provide a firm anchoring of the implant without incurring the risk that the roots 41 of the teeth 39 are damaged.

In a preferred embodiment of the implant, according the invention, said connecting piece 4 presents at least a first bend 42, this first bend 42 forming a support 43 for the connecting piece against the surface of the jawbone 5 when the implant 1 is fixed to this jawbone. Such an implant is represented in FIGS. 12 to 14. FIGS. 15 and 16 are showing such an implant that is fixed to, respectively, the lower or the upper jaw of a person.

Further, the implant advantageously has a second bend 44 in a direction opposite to said first bend 42. This second bend 44 is provided between the first bend 42 and said recesses 6,7 and 8 of the fastening means. When the implant is thus fixed to the jawbone a free space 45 is maintained between this second bend 44 and the jawbone 5.

During fixing of the fastening means to the bone of the jaw these means are gradually tightened against the jawbone by means of screws whereby simultaneously said first bend 42 is moved towards said jawbone until the bend 42 is firmly supported by the jawbone. Preferably, said second bend 44 is somewhat elastically extended such that the first bend 42 is applied with a pressing force against the jawbone.

In this way the connecting piece 4 remains stable when it is loaded through the mounting element 3 by orthodontic appliances. The presence of a support 43 between the connecting piece 4 and the jawbone prevents that the connecting piece is moving somewhat due to, for example, its limited elasticity.

Further, the mounting element 3 of the implant represented in the FIGS. 12 to 15 is different from the mounting element of the previous described implants, according to the invention.

As is shown in the FIGS. 12 to 15, the mounting element 3 comprises a tube 46 having a rectangular inner section 47. This tube 46 is extending perpendicular to the axis of bar forming the connecting piece 4. An orthodontic wire with, for example, a rectangular section can be inserted and fixed into this tube 46.

Further a hook 48 is fixed to the exterior wall of the tube 46 for attaching orthodontic appliances by means of, for example, a rubber band. The free end of this hook 48 is provided with a spherical element 49 having a diameter that is larger than the section of the hook 48.

The invention is by no means restricted to the above-described embodiments of the orthodontic implant according to the invention represented in the accompanying drawings. On the contrary, several variants are possible within the scope of the present invention, as far as the dimensions and shapes of the implant are concerned as well as the orthodontic appliances attached to it.

For example, these orthodontic appliances are not restricted to the brackets 15, the metal wire 16, the tension member 29 and the spiral springs 25, 28 and 32 described above, but they also comprise all the other usual orthodontic elements which can be placed in the oral cavity in order to adjust the position of certain teeth.

Moreover, the implant cannot only be connected to a brace with brackets, it can also work in conjunction with any type of braces.

Although a mounting element 3 has been described having a recess 17 working in conjunction with a bolt 22 for fixing a tie-bar 14 or other orthodontic appliances, several variants are possible. Thus, the tie-bar 14 can for example be fixed to the mounting element by means of gluing or via a clamped joint.

It is also possible for the mounting element 3 to be mounted directly to the metal wire 16, or to other orthodontic appliances, in order to avoid the use of a tie-bar 14.

In certain cases, it may be interesting to provide several recesses 17 in one and the same mounting element 3, such that several coupling rods 14 can be fixed to one and the same implant 1.

Further, the shape of the fastening means 2 is not restricted, of course, to an osteosynthesis plate with four recesses, but it can have all sorts of shapes, and possibly more or less recesses and corresponding screws. Thus, the fastening means 2 can for example be formed of a small threaded rod which is screwed directly in the jaw bone.

The invention claimed is:

1. Implant with fastening means (2) to be fixed to the bone of a person's upper jaw (5) or lower jaw (30), comprising
a mounting element (3) for mounting orthodontic appliances, whereby said mounting element (3) is connected to fastening means (2) by means of a connecting piece (4) formed by a rod with a circular section or an elliptic section, which is adapted to extend through the person's gum surrounding the corresponding bone to which said fastening means (2) are intended to be fixed, whereby said fastening means (2) are formed of an osteosynthesis plate which is provided with several recesses (6,7,8,9) through which fit screws (10,11,12,13) for fixing the implant to the bone of said upper or lower jaw, wherein said connecting piece (4) forms an extension of the osteosynthesis plate, wherein said connecting piece presents:
at least a first bend, this first bend forming a support for the connecting piece against the jawbone when the implant is fixed to this jawbone; and
a second bend in a direction opposite to said first bend is provided between the first bend and said recesses (6,7, 8,9) such that when the implant is fixed to the jawbone a free space is maintained between the second bend and the jawbone.

2. Implant according to claim 1, wherein the implant is adapted to be fixed to the lower side of the bone connecting the person's upper jaw to the zygoma such that the mounting element is situated in the person's oral cavity between the jawbone and the cheek.

3. Implant according to claim 1, wherein said recesses (6,7,8,9) which are provided in the osteosynthesis plate successively extend according to a longitudinal direction of said rod forming the connecting piece (4).

4. Implant according to claim 1, wherein the fastening means (2), the mounting element (3) and said rod forming the connecting piece (4) are made of in one piece and are milled out of one piece of metal.

5. Implant according to claim 1, wherein said mounting element has a hook for fixing orthodontic appliances.

6. Implant according to claim 5, wherein a free end of said hook is provided with a spherical element having a diameter that is larger than the section of the hook.

7. Implant according to claim 1, wherein said implant is made of titanium or of a titanium alloy.

* * * * *